United States Patent
Petersen

(12) United States Patent (10) Patent No.: US 7,517,358 B2
Petersen (45) Date of Patent: Apr. 14, 2009

(54) IMPLANT DEVICE USED IN MINIMALLY INVASIVE FACET JOINT HEMI-ARTHROPLASTY

(75) Inventor: David A. Petersen, Clearwater, FL (US)

(73) Assignee: Orthopedic Development Corporation, Clearwater, FL (US)

( * ) Notice: Subject to any disclaimer, the term of this patent is extended or adjusted under 35 U.S.C. 154(b) by 140 days.

(21) Appl. No.: 11/177,467

(22) Filed: Jul. 8, 2005

(65) Prior Publication Data

US 2006/0111781 A1 May 25, 2006

Related U.S. Application Data

(63) Continuation-in-part of application No. 10/992,746, filed on Nov. 22, 2004, now abandoned.

(51) Int. Cl.
*A61B 17/70* (2006.01)
(52) U.S. Cl. .............. 606/247; 606/246; 606/279; 623/17.11
(58) Field of Classification Search ............ 606/61, 606/69–71, 246–249, 279, 281–299; 623/17.11–17.16
See application file for complete search history.

(56) References Cited

U.S. PATENT DOCUMENTS

| 4,344,190 | A | 8/1982 | Lee et al. |
|---|---|---|---|
| 4,501,269 | A | 2/1985 | Bagby |
| 4,654,314 | A | 3/1987 | Takagi et al. |
| 4,737,411 | A | 4/1988 | Graves, Jr. et al. |
| 4,743,256 | A | 5/1988 | Brantigan |
| 4,834,757 | A | 5/1989 | Brantigan |
| 4,878,915 | A | 11/1989 | Brantigan |
| 4,961,740 | A | 10/1990 | Ray et al. |
| 4,990,161 | A | 2/1991 | Kampner |
| 5,009,666 | A | 4/1991 | Van Syckle et al. |
| 5,015,247 | A | 5/1991 | Michelson |
| 5,026,373 | A | 6/1991 | Ray et al. |
| 5,152,791 | A | 10/1992 | Hakamatsuka et al. |
| 5,298,254 | A | 3/1994 | Prewett et al. |
| 5,425,772 | A | 6/1995 | Brantigan |
| 5,571,191 | A | 11/1996 | Fitz |
| 5,593,409 | A | 1/1997 | Mechelson |
| 5,645,598 | A | 7/1997 | Brosnahan, III |
| 5,683,391 | A | 11/1997 | Boyd |

(Continued)

OTHER PUBLICATIONS

Stein, M. et al., Percutaneous Facet Joint Fusion: Preliminary Experience, J. Vasc. Interv. Radiol., Jan.-Feb. 1993, 4(1) 69-74.

*Primary Examiner*—Eduardo C Robert
*Assistant Examiner*—Andrew Yang
(74) *Attorney, Agent, or Firm*—Sheppard, Mullin, Richter & Hampton LLP

(57) ABSTRACT

A metallic inverted L-shaped implant is used to resurface the superior facet of the inferior vertebrae limited to the facet joints located on the spine, Occiput-C1 through L5-S1. The metallic implant is highly polished on its exterior and textured on its interior surface. It is mechanically crimped in place without the use of cement or pedicle screws. Permanent fixation occurs when bone in-grows onto a rough, porous surface on the inside of the implant. The implant employed in a hemi-arthroplasty method resurfaces half of the facet joint to provide for smooth, pain free joint articulation in deteriorated or diseased spinal facet joints without the need for major surgery or rehabilitation at considerably less risk to the patient.

17 Claims, 6 Drawing Sheets

U.S. PATENT DOCUMENTS

| | | | |
|---|---|---|---|
| 5,709,683 A | 1/1998 | Bagby | |
| 5,769,897 A | 6/1998 | Harle | |
| 5,782,919 A | 7/1998 | Zdeblick et al. | |
| 5,785,710 A | 7/1998 | Michelson | |
| 5,814,084 A | 9/1998 | Grivas et al. | |
| 5,860,973 A | 1/1999 | Michelson | |
| 5,865,846 A * | 2/1999 | Bryan et al. | 128/898 |
| 5,897,556 A | 4/1999 | Drewry et al. | |
| 5,899,939 A | 5/1999 | Boyce et al. | |
| 5,906,616 A | 5/1999 | Pavlov et al. | |
| 5,968,098 A | 10/1999 | Winslow | |
| 5,984,922 A | 11/1999 | McKay | |
| 6,033,438 A | 3/2000 | Bianchi et al. | |
| 6,045,580 A | 4/2000 | Scarborough et al. | |
| 6,053,916 A | 4/2000 | Moore | |
| RE36,758 E | 6/2000 | Fitz | |
| 6,083,225 A | 7/2000 | Winslow et al. | |
| 6,096,081 A | 8/2000 | Grivas et al. | |
| 6,111,164 A | 8/2000 | Rainey et al. | |
| 6,113,637 A | 9/2000 | Gill et al. | |
| 6,117,174 A | 9/2000 | Nolan | |
| 6,118,043 A | 9/2000 | Nies et al. | |
| 6,123,731 A | 9/2000 | Boyce et al. | |
| 6,132,464 A | 10/2000 | Martin | |
| 6,143,033 A | 11/2000 | Paul et al. | |
| 6,149,651 A | 11/2000 | Drewry et al. | |
| 6,224,630 B1 | 5/2001 | Bao et al. | |
| 6,241,770 B1 | 6/2001 | Michelson | |
| 6,241,771 B1 | 6/2001 | Gresser et al. | |
| 6,258,125 B1 | 7/2001 | Paul et al. | |
| 6,261,586 B1 | 7/2001 | McKay | |
| 6,264,656 B1 | 7/2001 | Michelson | |
| 6,270,528 B1 | 8/2001 | McKay | |
| 6,302,913 B1 | 10/2001 | Ripamonti et al. | |
| 6,315,795 B1 | 11/2001 | Scarborough et al. | |
| 6,346,123 B1 | 2/2002 | McKay | |
| 6,371,988 B1 | 4/2002 | Pafford et al. | |
| 6,371,989 B1 | 4/2002 | Chauvin et al. | |
| 6,375,655 B1 | 4/2002 | Zdeblick et al. | |
| 6,395,035 B2 | 5/2002 | Bresina et al. | |
| 6,398,811 B1 | 6/2002 | McKay | |
| 6,409,765 B1 | 6/2002 | Bianchi et al. | |
| 6,419,703 B1 | 7/2002 | Fallin et al. | |
| 6,432,436 B1 | 8/2002 | Gertzman et al. | |
| 6,440,444 B2 | 8/2002 | Boyce et al. | |
| 6,443,987 B1 | 9/2002 | Bryan | |
| 6,491,724 B1 | 12/2002 | Ferree | |
| 6,494,883 B1 | 12/2002 | Ferree | |
| 6,500,205 B1 | 12/2002 | Michelson | |
| 6,500,206 B1 | 12/2002 | Bryan | |
| 6,511,509 B1 | 1/2003 | Ford et al. | |
| 6,537,320 B1 | 3/2003 | Michelson | |
| 6,544,289 B2 | 4/2003 | Wolfinbarger, Jr. et al. | |
| 6,548,569 B1 | 4/2003 | Williams et al. | |
| 6,551,995 B1 | 4/2003 | Oppermann et al. | |
| 6,565,605 B2 | 5/2003 | Goble et al. | |
| 6,579,319 B2 | 6/2003 | Goble et al. | |
| 6,582,431 B1 | 6/2003 | Ray | |
| 6,585,770 B1 | 7/2003 | White et al. | |
| 6,610,091 B1 | 8/2003 | Reiley | |
| 6,613,091 B1 | 9/2003 | Zdeblick et al. | |
| 6,626,945 B2 | 9/2003 | Simon et al. | |
| 6,632,246 B1 | 10/2003 | Simon et al. | |
| 6,638,309 B2 | 10/2003 | Bonutti | |
| 6,641,613 B2 | 11/2003 | Sennett | |
| 6,645,206 B1 | 11/2003 | Zdeblick et al. | |
| 6,652,584 B2 | 11/2003 | Michelson | |
| 6,652,592 B1 | 11/2003 | Grooms et al. | |
| 6,689,167 B2 | 2/2004 | Bagby | |
| 6,695,882 B2 | 2/2004 | Bianchi et al. | |
| 6,696,073 B2 | 2/2004 | Boyce et al. | |
| 6,702,856 B2 | 3/2004 | Bonutti | |
| 6,709,458 B2 | 3/2004 | Michelson | |
| 6,719,795 B1 | 4/2004 | Cornwall et al. | |
| 6,743,255 B2 | 6/2004 | Ferree | |
| 6,747,121 B2 | 6/2004 | Gogolewski | |
| 6,758,849 B1 | 7/2004 | Michelson | |
| 6,790,233 B2 | 9/2004 | Brodke et al. | |
| 6,793,679 B2 | 9/2004 | Michelson | |
| 6,814,756 B1 | 11/2004 | Michelson | |
| 6,827,740 B1 | 12/2004 | Michelson | |
| 6,838,493 B2 | 1/2005 | Williams et al. | |
| 6,840,961 B2 | 1/2005 | Tofighi et al. | |
| 6,843,807 B1 | 1/2005 | Boyce et al. | |
| 6,852,125 B2 | 2/2005 | Simon et al. | |
| 6,867,247 B2 | 3/2005 | Williams et al. | |
| 6,893,462 B2 | 5/2005 | Buskirk et al. | |
| 6,905,517 B2 | 6/2005 | Bonutti | |
| 6,923,810 B1 | 8/2005 | Michelson | |
| 6,972,035 B2 | 12/2005 | Michelson | |
| 6,986,788 B2 | 1/2006 | Paul et al. | |
| 6,989,029 B2 | 1/2006 | Bonutti | |
| 7,001,385 B2 | 2/2006 | Bonutti | |
| 7,008,453 B1 | 3/2006 | Michelson | |
| 7,012,034 B2 | 3/2006 | Heide et al. | |
| 7,044,968 B1 | 5/2006 | Yaccarino, III et al. | |
| 7,048,762 B1 | 5/2006 | Sander et al. | |
| 7,056,342 B2 | 6/2006 | Michelson | |
| 7,060,096 B1 | 6/2006 | Schopf et al. | |
| 7,077,866 B2 | 7/2006 | Gresser et al. | |
| 7,087,082 B2 | 8/2006 | Paul et al. | |
| 7,087,540 B2 | 8/2006 | Heide et al. | |
| 7,105,023 B2 | 9/2006 | Eckman | |
| 7,118,598 B2 | 10/2006 | Michelson | |
| 2001/0020186 A1 | 9/2001 | Boyce et al. | |
| 2001/0034553 A1 | 10/2001 | Michelson | |
| 2001/0039458 A1 | 11/2001 | Boyer, II et al. | |
| 2001/0043940 A1 | 11/2001 | Boyce et al. | |
| 2001/0049560 A1 | 12/2001 | Paul et al. | |
| 2002/0029081 A1 | 3/2002 | Scarborough et al. | |
| 2002/0062153 A1 | 5/2002 | Paul et al. | |
| 2002/0082700 A1 | 6/2002 | Bianchi et al. | |
| 2002/0272806 | 6/2002 | Buskirk et al. | |
| 2002/0111680 A1 | 8/2002 | Michelson | |
| 2002/0128715 A1 * | 9/2002 | Bryan et al. | 623/17.15 |
| 2002/0151895 A1 * | 10/2002 | Soboleski et al. | 606/61 |
| 2003/0009235 A1 | 1/2003 | Manrique et al. | |
| 2003/0028250 A1 | 2/2003 | Reiley et al. | |
| 2003/0050701 A1 | 3/2003 | Michelson | |
| 2003/0100949 A1 | 5/2003 | Michelson | |
| 2003/0144736 A1 | 7/2003 | Sennett | |
| 2004/0059425 A1 | 3/2004 | Schmiedling | |
| 2004/0073309 A1 | 4/2004 | Bianchi et al. | |
| 2004/0138748 A1 | 7/2004 | Boyer, II et al. | |
| 2004/0148029 A1 | 7/2004 | Bianchi et al. | |
| 2004/0176771 A1 | 9/2004 | Schmieding | |
| 2004/0176772 A1 | 9/2004 | Zubok et al. | |
| 2004/0186571 A1 | 9/2004 | Brau et al. | |
| 2004/0230303 A1 | 11/2004 | Gomes et al. | |
| 2005/0004672 A1 | 1/2005 | Pafford et al. | |
| 2005/0159746 A1 * | 7/2005 | Grob et al. | 606/61 |
| 2005/0165483 A1 | 7/2005 | Ray, III et al. | |
| 2005/0177240 A1 * | 8/2005 | Blain | 623/17.15 |
| 2005/0216081 A1 * | 9/2005 | Taylor | 623/17.11 |
| 2005/0216083 A1 | 9/2005 | Michelson | |
| 2005/0222687 A1 | 10/2005 | Vunjak-Novakovic et al. | |
| 2005/0267578 A1 | 12/2005 | Michelson | |
| 2006/0036243 A1 * | 2/2006 | Sasso et al. | 606/61 |
| 2006/0041311 A1 * | 2/2006 | McLeer | 623/17.11 |
| 2006/0106381 A1 | 5/2006 | Ferree et al. | |
| 2006/0111779 A1 | 5/2006 | Petersen | |
| 2006/0173543 A1 | 8/2006 | Brau et al. | |

* cited by examiner

IMPLANT DEVICE USED IN MINIMALLY INVASIVE FACET JOINT HEMI-ARTHROPLASTY

PRIOR APPLICATION

This application is a continuation-in-part from application Ser. No. 10/992,746, filed Nov. 22, 2004 now abandoned.

BACKGROUND OF THE INVENTION

The present invention relates generally to a device for use in minimally invasive spine surgery. More particularly, it refers to a pre-made, pre-shaped metallic implant implanted using an arthroscopic type portal or classic open surgical method to achieve a spinal facet joint hemi-arthroplasty to resurface any or all of the forty-eight superior facets of the inferior Occiput-C1 through L5-S1 vertebrae.

In the United States alone, about 10% of the entire population will suffer from back pain sometime in the next twelve months. More people will contract back pain in the next year than any other injury or disease except the common cold and flu. About one-third will not recover and have to live with persistent, disabling symptoms. The number is cumulative year after year.

One of the root causes of back pain, particularly persistent and disabling back pain, are facet joints, small joints located behind adjacent vertebrae in the spine that allow for spinal motion.

Present surgical solutions available for the millions of people with facet joint dysfunctions are complex, invasive, high-risk operations requiring pedicle screws for fixation and significant reduction or elimination of natural joints and replacement with prosthetic apparatus such as those described in U.S. Pat. Nos. 6,610,091, 6,579,319, 6,132,464, 6,113,637 and U.S. Patent Application 2003/0028250. In general, the present art requires prolonged recovery times, from six to twenty-four months, and offers uncertain outcomes. High risk equates to frequent litigation, which forces non-surgical symptomatic treatment while the disease or consequences of injury progressively worsen.

With the advent of new, safer and less invasive surgical techniques and technology, the growth of spine surgery now outpaces every other orthopedic surgery segment. Its growth is further fueled by an enormous demand. Improvements in devises used in spinal joints is needed.

SUMMARY OF THE INVENTION

The present invention provides a pre-made pre-shaped metallic implant for use in minimally invasive spine surgery. The use of a pre-shaped metallic overlay of this invention for facet joint resurfacing of diseased, painful, deteriorated or overstressed joints offers three distinct advantages over larger prosthetic implants; namely, (1) using a thin metallic overlay allows for minimally invasive insertion that is safer, less traumatic and requires far less recovery time compared to a prosthetic; (2) the overlay does not require the use of cements, pedicle screws or other fixation methods that can work their way loose over time; and, (3) the implant has two fins or blades to provide lateral stability and two teeth to provide temporary fixation and a rough or porous inner surface amenable to bone in growth providing permanent natural fixation. The implant also has a polished outside that allows for smooth, natural, pain free articulation of the joint.

The implant is specifically designed for use in an arthroscopic type portal for standalone procedures, but also may be used in classic open surgery. This implant provides a unique, stronger and superior resurfacing and may be used for, but not limited to: (1) an adjunct to instrumented vertebral fusion when implanted in the two facet joints immediately above and below the two joints adjoining the instrumentation thereby eliminating the risk of collateral post-operative facet joint pain resulting from additional stress placed on facet joints, (2) when used to resurface adjoining facet joints directly above and below a disk replacement by eliminating the risk of collateral post-operative facet joint pain resulting from additional stress placed on facet joints by the disk replacement, and, (3) as a stand along treatment for diseased, painful or deteriorated facet joints.

The invention accomplishes its goal of resurfacing a painful, diseased or deteriorated spinal facet joints by providing a resurfacing implant to replace the joint surface with a small metal on bone overlay. The overlay, constructed of cobalt chrome or such other biocompatible metal or metallic alloy appropriate for joint hemi-arthroplasties, is one of several sizes for various segments of the spine, similarly sized for different facet joints or groups of joints in the spine and are attached to the joint using a straightforward process without the need for screws or cements. The facet joints may be accessed using an arthroscopic type portal eliminating the need for open surgery, hospitalization and long recovery periods. The procedure also may be performed as an adjunct to other procedures such as instrumented fusion and disc replacement in a traditional open surgery. Because the side of the implant that attaches to bone is porous, the bone heals onto it, permanently fixing it into place. A uniquely designed set of blades and teeth provides temporary fixation to the joint and prevents migration. A crimping system allows the implant to be fixed into place, holding it firmly until bone in growth is complete. The side making contact with the joint is highly polished providing a smooth, virtually frictionless surface that undergoes virtually no wear and tear. The inside is rough or porous providing an amenable surface for bone in growth.

According to one broad aspect of the invention, a unique metallic prosthetic overlay is provided. The metallic overlay is generally shaped to the naturally shaped contour of the bone it resurfaces and is highly polished on the outside to provide frictionless articulation of the joint and rough or porous on the inside to promote and provide a surface to allow the natural bone to grow into the overlay, providing a permanent fixation. In the interim between implantation and bone in-growth, the overlay is mechanically crimped into place using two teeth opposed to each other and one to two blades on the inside of the implant that bite into the bone to prevent lateral migration. The overlay is further held into place by the natural pressure of the inferior and superior sides of the joint as they come together in their natural position.

The system to insert the prosthetic overlay includes any number of instruments allowing preparation of the joint and the implant to be placed using a minimally invasive surgical arthroscopic technique to access to the joint that include a director probe to determine the correct facet joint angle, a separator to assist with separation of the vertebrae to improve access to the joint, an osteotome to make a small cut in the bone to prepare the surface for the implant, a broach to prepare the bone to match the implant shape, an impactor to impact the implant into place and a crimp to fix the implant to prevent migration prior to healing and a unique implant. By way of example only, the director may include a planer blade or rasp to remove any bone spurs or overgrowth and to flatten the facet joint surface in preparation for implant placement.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein.

DETAILED DESCRIPTION OF THE INVENTION

Figure 1:
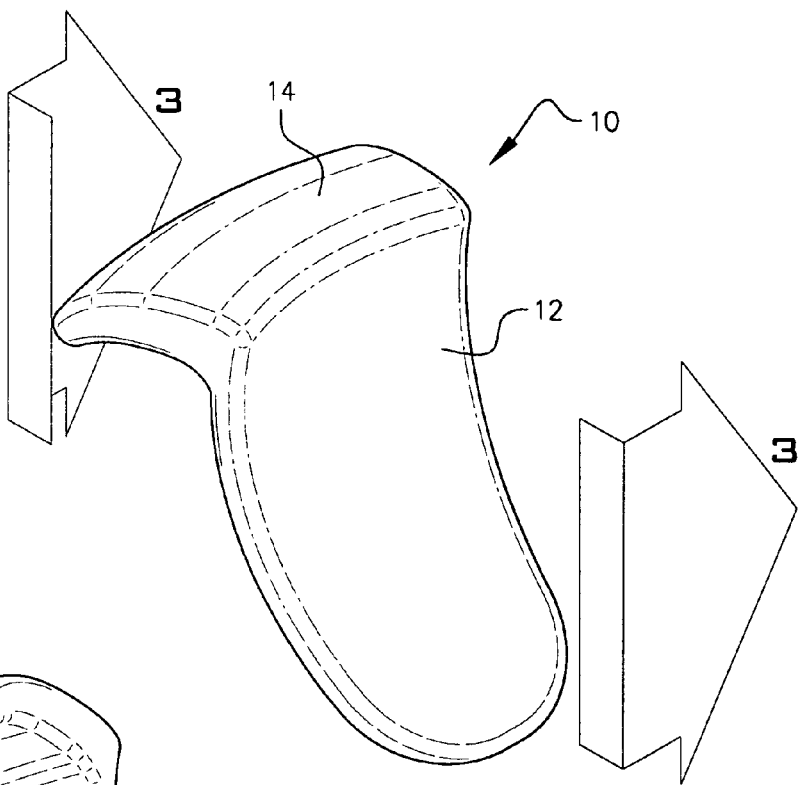
FIG. 1 shows a top right isometric view of the implant.
Figure 2:
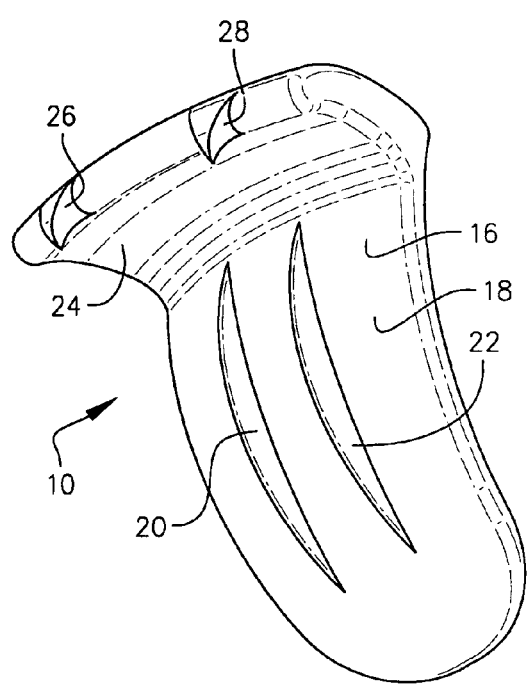
FIG. 2 shows a bottom left isometric view of the implant.
Figure 3:
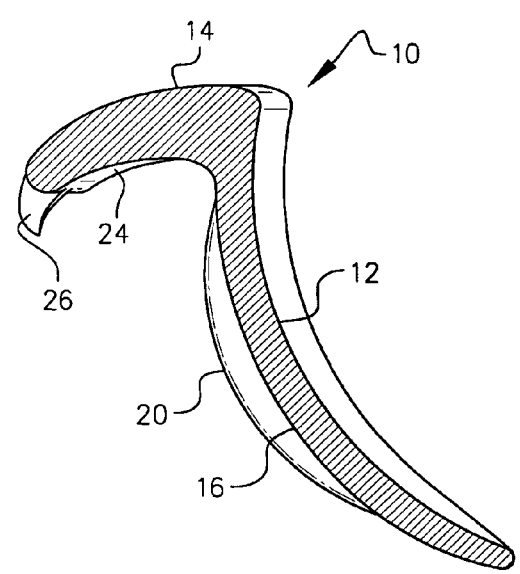
FIG. 3 shows a sectional view along line 3-3 of FIG. 1.
Figure 4:
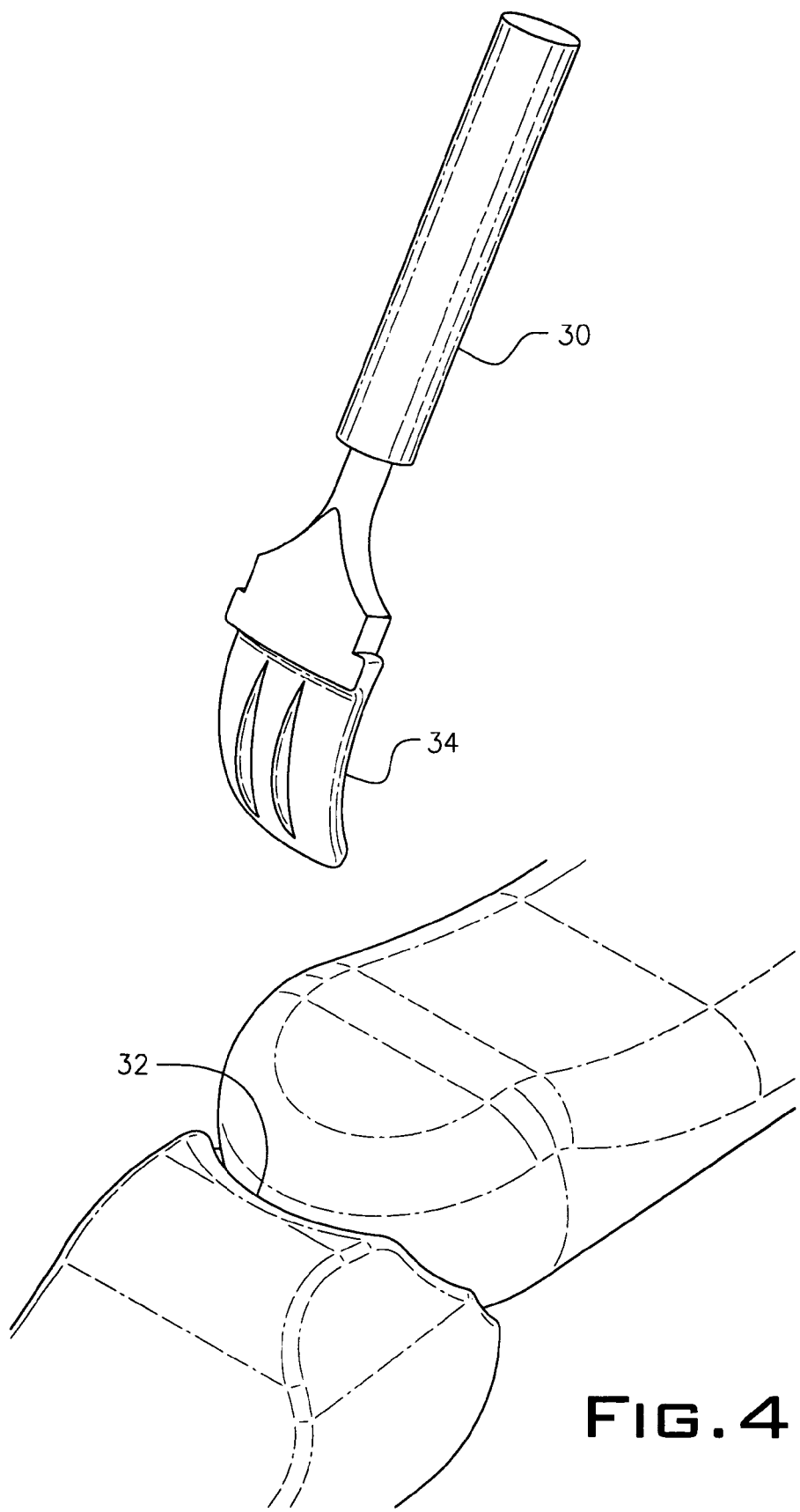
FIG. 4 shows a perspective view of a tool used to prepare the facet joint for receipt of the implant.
Figure 5:
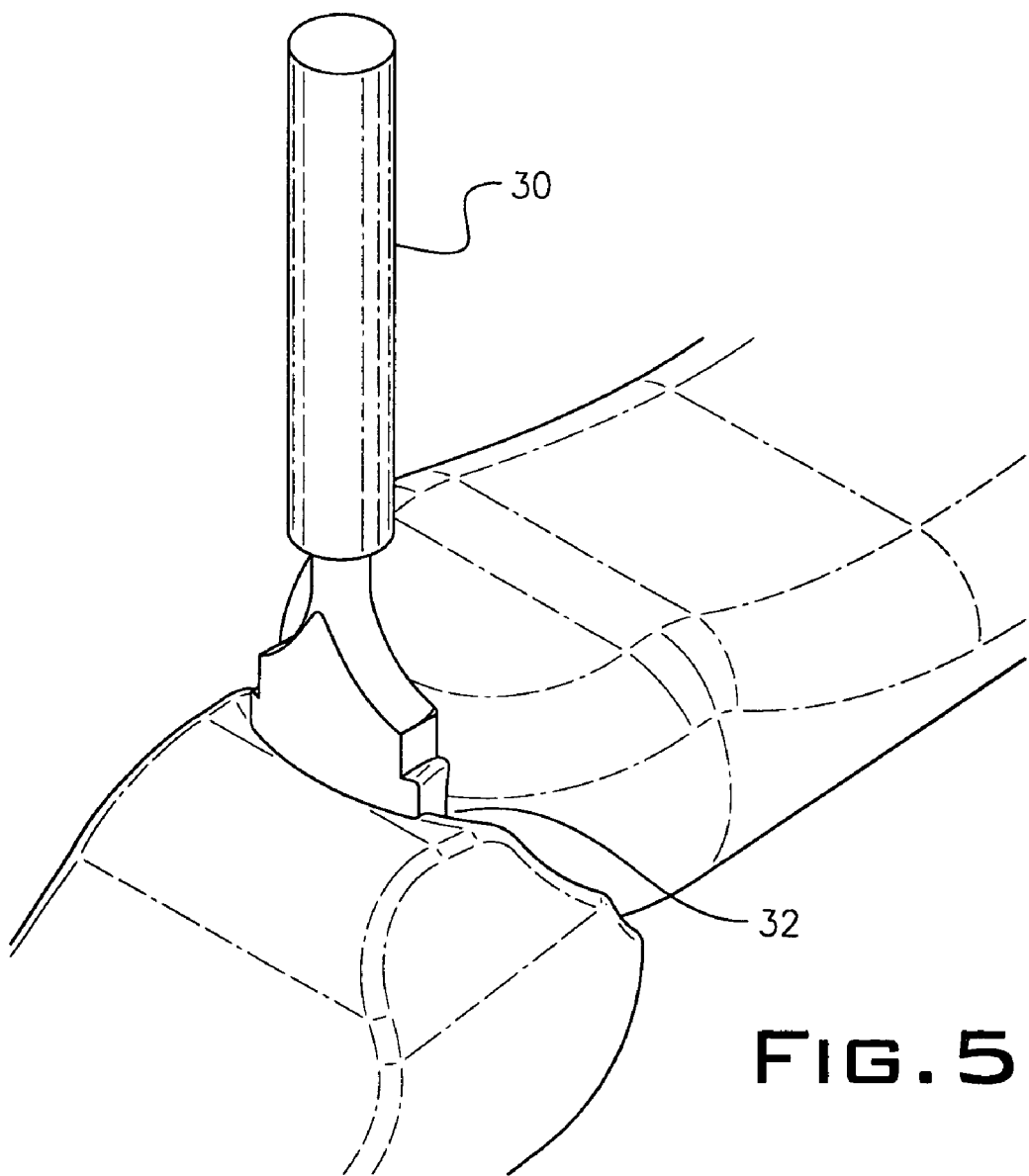
FIG. 5 shows the tool inserted in the facet joint.
Figure 6:
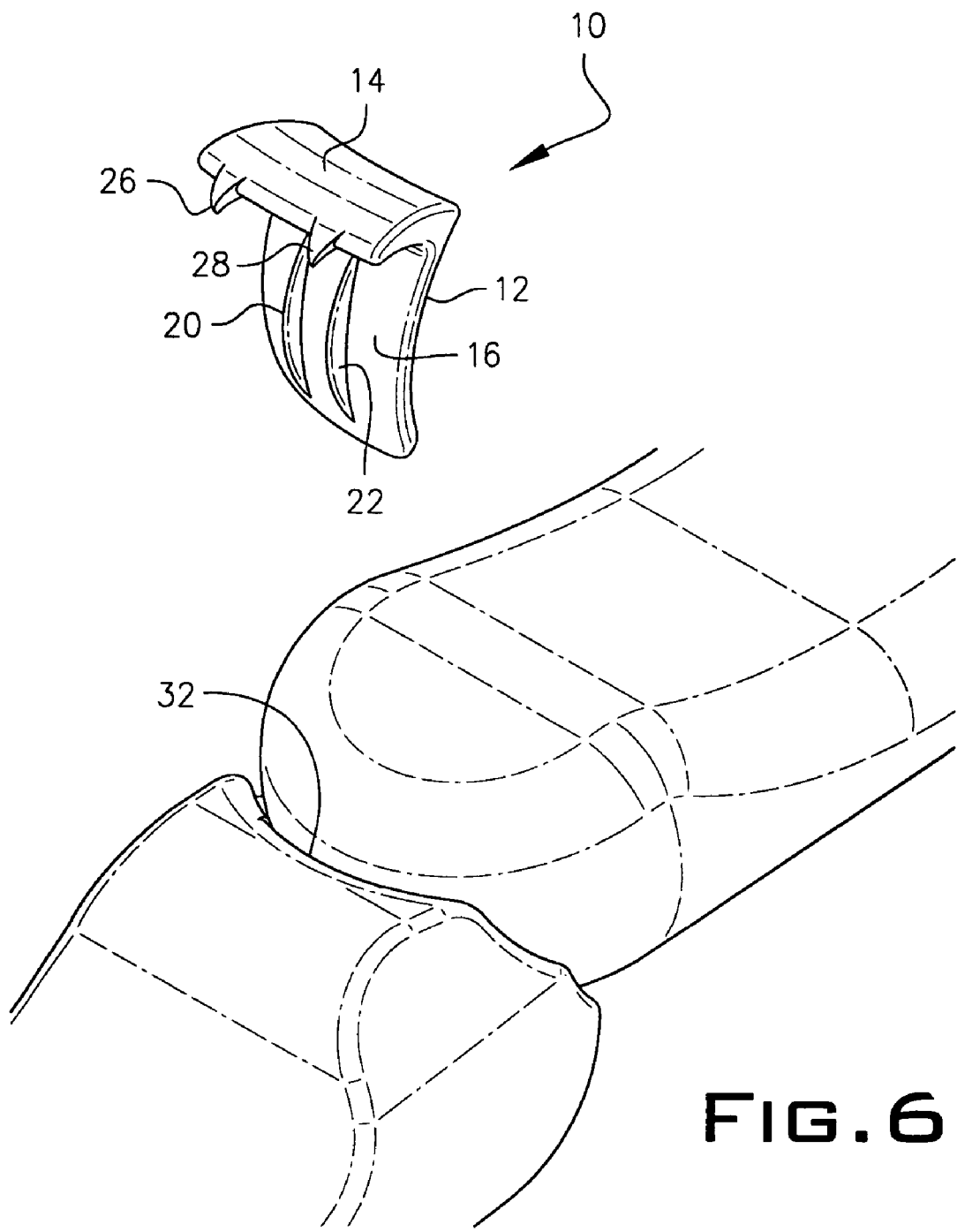
FIG. 6 shows the insert about to be installed in the facet joint.
Figure 7:
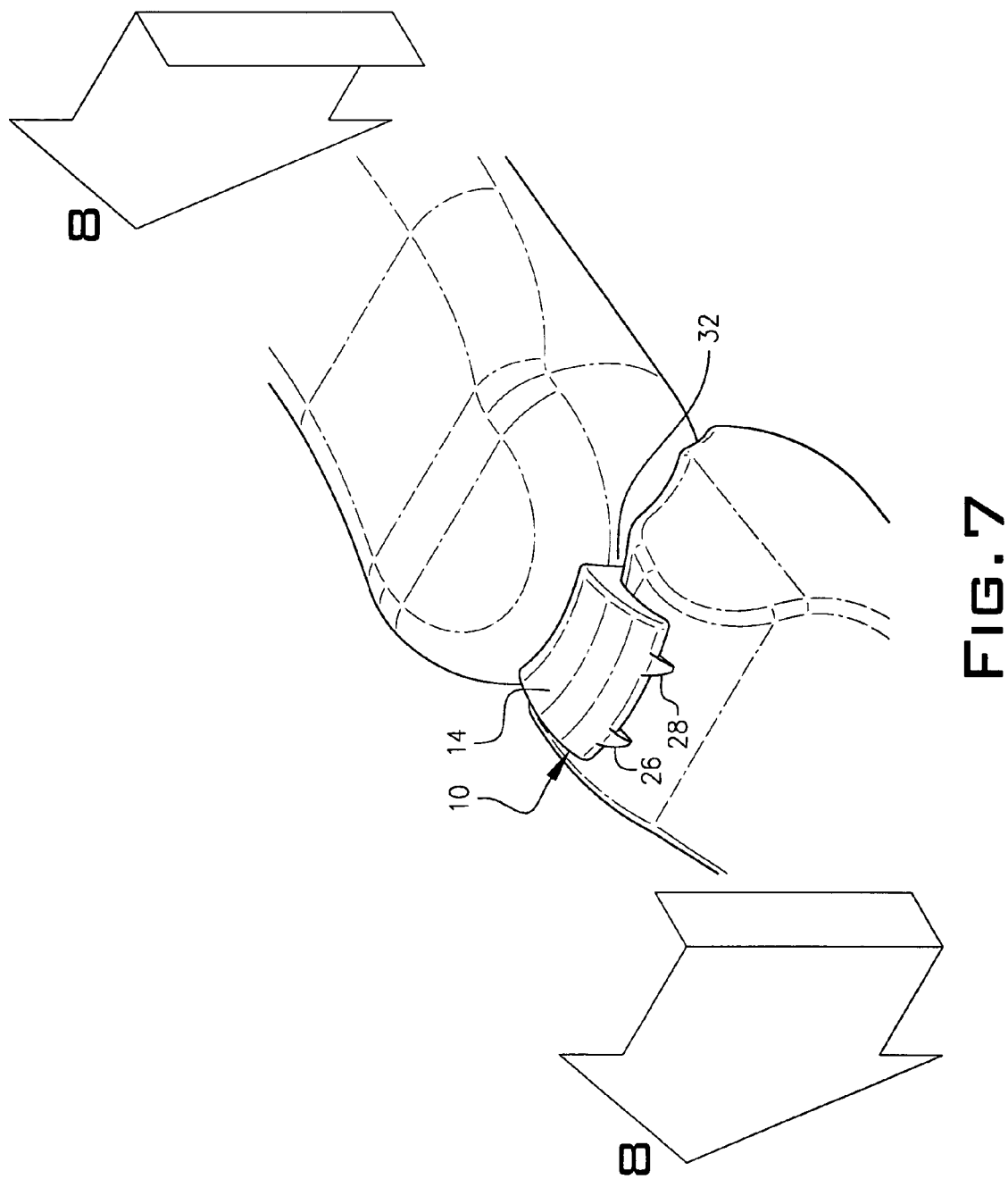
FIG. 7 shows the insert embedded in the facet joint.
Figure 8:
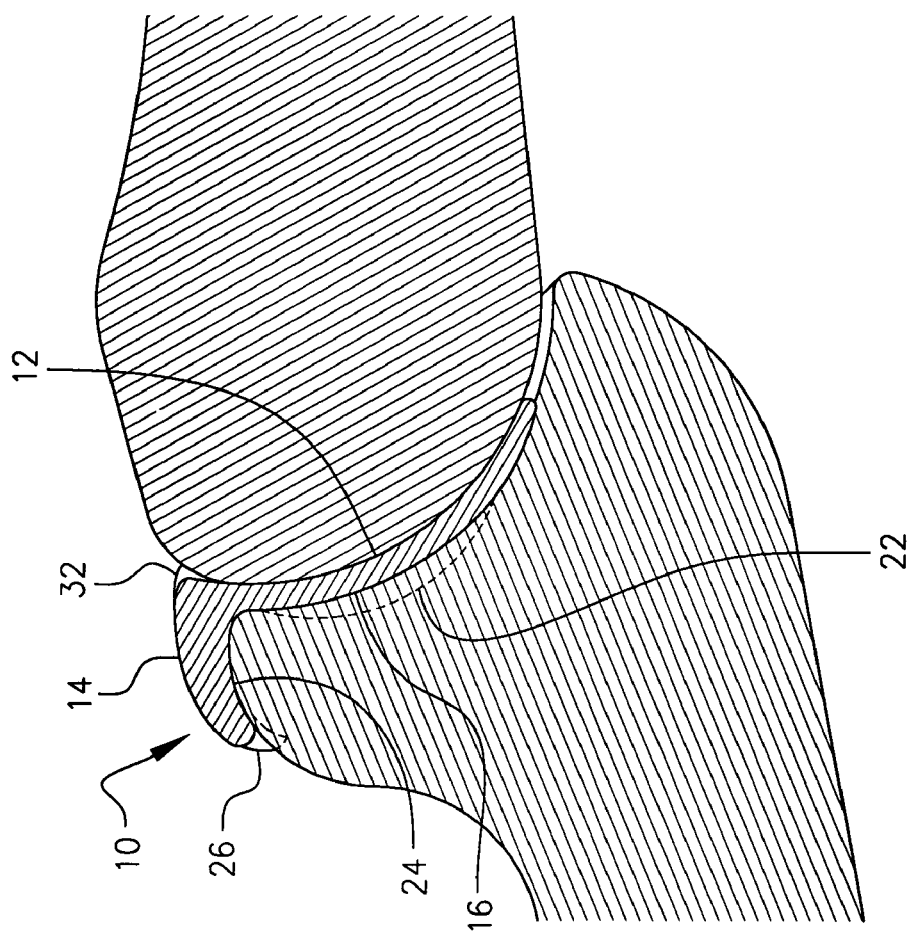
FIG. 8 shows a sectional view along line 8-8 in FIG. 7.

Referring to FIG. 1, the prosthetic implant 10 of this invention has a highly polished concave outside back portion 12 and a convex highly polished surface on a top portion 14. The highly polished surface is a cobalt-chrome alloy, a titanium alloy or other biologically acceptable material capable of forming a smooth highly polished surface. Referring to FIG. 2, an inside convex surface is textured 18 to encourage new bone growth and adhesion. Blades 20 and 22 attached to inside surface 16 bite into bone to promote adhesion. The bottom surface 24 of the top portion of implant 10 is concave to fit tightly over a bone as shown in FIGS. 7 and 8. Teeth 26 and 28 are used for imbedding into adjacent bone to prevent movement of implant 10.

Prior to imbedding the implant in the facet joint 32, a preparation tool 30 is used to slightly spread the joint 32. Tool end 34 is inserted into the joint 32 to provide sufficient space for inserting implant 10 into joint 32 as seen in FIGS. 7 and 8.

The use of the prosthetic implant 10 has two advantages over the prior art.

1. It is minimally invasive, low risk, fast (about 20 minutes per joint in an outpatient setting compared to about three hours in a hospital followed by a three day stay), and has a recovery time measured in a few weeks (compared to six to twenty-four months); and 2. It has a high success rate, does not preclude other surgical options, and is non-limiting and permanent.

The present invention is directed at overcoming, or at least improving upon, the disadvantages of the prior art by achieving the following:

Reversal of the risk/benefit ratio of the present procedures versus the invention;
A stand-alone minimally invasive procedure versus major open surgery;
Employed as an adjunct to major open surgery in concert with long fusion and with disc replacement surgery to strengthen adjacent facet joints.
Outpatient versus inpatient surgery (about 20 minutes per joint versus hours);
Reduced morbidity;
Reduced blood loss;
Reduced time under anesthesia;
Reduced risk;
Recovery time dramatically reduced;
Minimal scarring that decreases the risk of failed back syndrome and improves revisions surgery outcome;
Reduced risk of post operative infection by significantly reducing operating room time and soft tissue destruction;
Prolonging the functional life of long segment fusions and disc replacement.
No preclusion of other surgical or non-invasive treatment options; and,
Projected high success rate by utilizing accepted procedures facilitated through an arthroscopic technique and resurfacing implant.

It is anticipated that the availability of this method, instrumentation and implant will increase the number of surgeries performed because they offer the first safe outpatient solution to a predominant cause of joint pain. The inventor also expects that virtually all patients receiving this procedure will be able to walk the same day as surgery and be fully functional within a few weeks. Present surgical solutions require hospitalization of about three days and six to twenty-four months' recovery.

Aside from the obvious positive clinical outcome, the significant favorable financial impact on disability, worker's compensation and health care insurers is considerable.

Spinal facet implant units are calculated per joint. Each patient has two joints per spinal segment and six segments (T12 to L1 through L5-S1) in the lumbar spine, or twelve lumbar, fourteen cervical and twenty-eight thoracic joints. Each surgery is likely to involve multiple joints, with a probable average of four per patient.

The invention accomplishes its goal of reducing, preventing or eliminating spinal facet joint pain by providing a resurfacing implant to replace the joint surface with a small metal on bone overlay. The overlay, constructed of cobalt chrome, a material previously approved by the FDA for other joint hemi-arthroplasty, or such other metallic construction as may be safely used, is one of several sizes for various segments of the spine, may be similarly sized for different joints and is attached to the joint using a straightforward process without the need for screws or cements with the aid of custom designed instruments. The joint is accessed using an arthroscopic type portal eliminating the need for open surgery, hospitalization and long recovery periods (unless the procedure is performed as an adjunct to other procedures such as instrumented fusion and disc replacement in a traditional open surgery). Because the side that attaches to bone is porous, the bone heals onto it, permanently fixing it into place. A uniquely designed set of blades and teeth prepares the joint and a unique crimping system allows the implant to be fixed into place, holding it firmly until bone in growth is complete. The side making contact with the joint is highly polished providing a smooth, virtually frictionless surface that undergoes virtually no wear and tear. The resurfacing implant is a securely fixed porous hemi-arthroplasty of the facet joints of the spine.

The metallic overlay is generally shaped to the natural contour of the bone it resurfaces and is highly polished on the outside to provide frictionless articulation of the joint and rough and porous on the inside to promote and provide a surface to allow the natural bone to grow into the overlay, providing a permanent fixation. In the interim between implantation and bone in-growth, the overlay is mechanically crimpled into place using two teeth opposed to each other that bite into the bone to prevent migration. The overlay is further held into place by the natural pressure of the inferior and superior sides of the joint as they come together in their natural position.

The system includes any number of instruments 30 allowing preparation of the joint 32 and the implant 10 to be placed using a minimally invasive surgical arthroscopic technique to access to the joint that include a director probe to determine the correct facet joint angle, a separator to assist with separation of the vertebrae to improve access to the joint, an osteotome to make a small cut in the bone to prepare the surface for the implant, a broach to prepare the bone to match the implant shape, an impactor to impact the implant into place and a crimp to fix the implant to prevent migration prior to healing and a unique implant. By way of example only, the director may include a planer blade or rasp to remove any bone spurs or overgrowth and to flatten the facet joint surface in preparation for implant placement.

Equivalent elements can be substituted for the elements of the implant of this invention to provide substantially the same function in substantially the same way to achieve substantially the same result.

What is claimed is:

1. A method of performing minimally-invasive facet joint arthroplasty, said method comprising the step of:
    inserting an inverted L-shaped prosthetic implant into a facet-joint, said implant having:
        a metallic body having a convex top portion integral at a rear edge with a concave downwardly descending portion, the top and downwardly descending portions having a highly polished exterior surface of a material biocompatible with bone;
        a concave lower surface under the top portion and convex inner textured surface on the downwardly descending portion; and
        at least one blade integral with the convex inner textured surface and a pair of teeth descending from a front edge of the convex top portion, wherein the at least one blade is positioned and configured to provide lateral stability when the implant is inserted into the facet joint and wherein the pair of teeth provides temporary fixation of the implant into the bone when the implant is inserted.

2. The method of claim 1 wherein the highly polished exterior surface of the implant is a cobalt-chrome alloy.

3. The method of claim 1 wherein the highly polished exterior surface of the implant is a titanium alloy.

4. The method of claim 1 wherein the convex inner textured surface of the implant is porous and compatible with bone.

5. The method of claim 1 wherein the prosthetic implant comprises two blades integral with the convex inner textured surface, wherein the two blades are positioned and configured to provide lateral stability when the implant is inserted into the facet joint.

6. The method of claim 1 wherein the inserting step comprises mounting the implant within the facet joint such that the highly polished exterior surface is juxtaposed to oppositely positioned bones in the facet joint.

7. The method of claim 1 wherein the inserting step comprises mounting the implant within a facet joint such that the textured surface conforms to the shape of a juxtaposed bone.

8. The method of claim 5 wherein the inserting step comprises mounting the implant within a facet joint such that the textured surface conforms to the shape of a juxtaposed bone and the two blades cut into the juxtaposed bone, and wherein the two blades are positioned and configured to provide lateral stability when the implant is inserted into the facet joint.

9. The method of claim 1 wherein the inserting step comprises employing a director probe to determine the correct facet joint angle.

10. The method of claim 1 further comprising the step of crimping the implant into place in the facet joint.

11. The method of claim 10 wherein the crimping step comprises pressing the pair of teeth downwardly into the bone.

12. The method of claim 10 wherein the crimping step comprises employing an impactor to impact the implant into place in the facet joint.

13. The method of claim 10 wherein the crimping step is accomplished without the use of screws or cement.

14. A method of performing minimally-invasive facet joint arthroplasty, said method comprising the steps of:
    inserting an inverted L-shaped prosthetic implant into a facet joint, said implant having;
        a metallic body having a convex top portion integral at a rear edge with a concave downwardly descending portion, the top and downwardly descending portions having a highly polished exterior surface of a material biocompatible with bone;
        a concave lower surface under the top portion and convex inner textured surface on the downwardly descending portion; and
        at least one blade integral with the convex inner textured surface and
        a pair of teeth descending from a front edge of the convex top portion;
    wherein the inserting step comprises mounting the implant within the facet joint such that the highly polished exterior surface is juxtaposed to oppositely positioned bones in the facet joint and such that the textured surface conforms to the shape of a juxtaposed bone, wherein the at least one blade is positioned and configured to provide lateral stability when the implant is inserted into the facet joint and wherein the pair of teeth provides temporary fixation of the implant into the bone when the implant is inserted into the facet joint; and
    crimping said implant into place in the facet joint.

15. The method of claim 14 wherein the highly polished exterior surface of the implant is a cobalt-chrome alloy.

16. The method of claim 14 wherein the highly polished exterior surface of the implant is a titanium alloy.

17. The method of claim 14 wherein the convex inner textured surface of the implant is porous and compatible with bone.

* * * * *